United States Patent [19]
Felblinger et al.

[11] Patent Number: 5,782,241
[45] Date of Patent: Jul. 21, 1998

[54] SENSOR DEVICE FOR ELECTROCARDIOGRAM

[75] Inventors: Jacques Felblinger, Toffen; Chris Boesch, Thun, both of Switzerland; Gerard Muller, Rohrbach les Bitche; Michel Kraemer, Durrenbach, both of France

[73] Assignee: O.D.A.M. Office de Distribution d'Appareils Medicaux (SA), Wissembourg, France

[21] Appl. No.: 537,786

[22] PCT Filed: Apr. 21, 1994

[86] PCT No.: PCT/FR94/00454

§ 371 Date: Oct. 23, 1995

§ 102(e) Date: Oct. 23, 1995

[87] PCT Pub. No.: WO94/23648

PCT Pub. Date: Oct. 27, 1994

[30] Foreign Application Priority Data

Apr. 22, 1993 [FR] France ............... 93 04918

[51] Int. Cl.$^6$ .................................. A61B 5/0428
[52] U.S. Cl. .............................. 128/696; 128/908
[58] Field of Search ........................ 128/696, 907, 128/908

[56] References Cited

U.S. PATENT DOCUMENTS

| | | | |
|---|---|---|---|
| 3,757,778 | 9/1973 | Graham | 128/696 |
| 3,910,257 | 10/1975 | Fletcher et al. | 128/908 |
| 4,041,954 | 8/1977 | Ohara | 128/908 |
| 4,181,134 | 1/1980 | Mason et al. | |
| 4,245,649 | 1/1981 | Schmidt-Andersen | 128/696 |
| 4,375,219 | 3/1983 | Schmid | 128/639 |
| 4,858,617 | 8/1989 | Sanders | 128/696 |
| 5,217,010 | 6/1993 | Tsitlik et al. | 128/696 |

FOREIGN PATENT DOCUMENTS

| | | |
|---|---|---|
| 0 132 785 | 2/1985 | European Pat. Off. |
| 0 170 448 | 2/1986 | European Pat. Off. |
| 0 173 130 | 3/1986 | European Pat. Off. |
| 0 178 990 | 4/1986 | European Pat. Off. |
| 0 498 996 | 8/1992 | European Pat. Off. |
| WO 88/05282 | 7/1988 | WIPO |

*Primary Examiner*—William E. Kamm
*Attorney, Agent, or Firm*—Young & Thompson

[57] ABSTRACT

A sensor device intended to be implemented at the vicinity or inside a nuclear magnetic resonance apparatus, and more particularly on a patient inside the canal of the magnet of a magnetic resonance imager (MRI). The device includes at least two non-metal electrodes intended to be applied to the skin of a patient, and an electro-optical conversion, amplification and filtering module for the electric signals received from the heart by the electrodes. The module is arranged in a shielded casing forming a Faraday cage, and optically connected to a display and/or monitoring apparatus. A support body made of non-magnetic material carries the electrode and the shielded casing containing the module.

9 Claims, 3 Drawing Sheets

SENSOR DEVICE FOR ELECTROCARDIOGRAM

BACKGROUND OF THE INVENTION

The present invention relates to the field of receiving and measuring biological signals and the surveillance of patients, particularly patients undergoing nuclear magnetic resonance (NMR) examination for example in a magnetic resonance imager (MRI), and has for its object a detector device for electrocardiograms.

BACKGROUND OF THE INVENTION

At present, electrocardiogram signals from patients subjected to an NMR examination are received by means of electrodes with metallic conductors and transmitted to a visualization and/or surveillance apparatus disposed in the shielded enclosure or outside, by means of electric cables of great length, as the case may be shielded and twisted together.

However, these electrical cables, forming antennas, disturb the electromagnetic environment of the NMR apparatus and render false the measurements and, in the case of an imager, the virtual reconstructions (images) obtained by this latter.

Conversely, the field gradients, the radiofrequency fields and the phenomena connected to switching between emitting and receiving coils in the course of an experiment of the NMR type greatly disturb the transmission of the low power signals received at the heart and may, by generation of important false images, render these latter totally unusable, even though the patient is disposed within the interior of the principal magnet of the NMR apparatus.

Moreover, possible movements of the patient (particularly breathing) give rise to movements of said electrical transmission cables in the existing field, from which automatically results an induction of voltages generating false images.

Moreover, the troublesome phenomena described are greatly amplified when the transmission cables have one or several loops.

Thus, the energy stored by the cable or cables, subjected to high intensity electromagnetic fields, at said loops or cable, can be fairly great so as to provoke substantial heating of said cable, which can give rise to burns on the patient's skin on which a portion of the cables rest, particularly when passing through an emission antenna.

Moreover, the placement of the electrodes on the patient in the region of the heart requires, for correct emplacement, the intervention of a specialist, each of said electrodes having to be precisely positioned individually.

It has been proposed, in an attempt to overcome certain of these drawbacks, to use algorithms for correcting the false images generated by the gradients and the radiofrequency fields.

However, these algorithms are not adapted to other than a predetermined type of NMR apparatus, with a given configuration of windings and frequently with a particular NMR sequence, which results in a great loss of flexibility during their application.

Moreover, they do not permit solving the problems of burns, nor the problems of induction of voltage because of the movements of the cables or again the problems of positioning the electrodes.

SUMMARY OF THE INVENTION

The present invention has particularly for its object to relieve all of the recited drawbacks, by simple means, not burdensome and of general application, no matter what the type of apparatus used.

To this end, it has for its object a detector device for electrocardiograms, adapted to be used in a charged and sensitive electromagnetic environment, particularly adjacent or within an NMR apparatus, and more particularly on a patient within the tunnel of the magnet of an NMI, characterized in that it is principally constituted, on the one hand, by at least two non-metallic electrodes, adapted to be applied to the skin of a patient, on the other hand, by a module for filtering and amplifying and electro-optically converting electrical signals from the heart, received by means of said receiving electrodes, disposed in a shielded casing forming a Faraday cage and connected by optical means to a visualization and/or control apparatus and, finally, by a support body of an amagnetic material, bearing the electrodes and the shielded casing containing the module.

BRIEF DESCRIPTION OF THE DRAWINGS

The invention will be better understood from the following description, which relates to a preferred embodiment, given by way of non-limiting example, and explained with reference to the accompanying schematic drawings, in which.

DETAILED DESCRIPTION OF THE INVENTION

Figure 1:
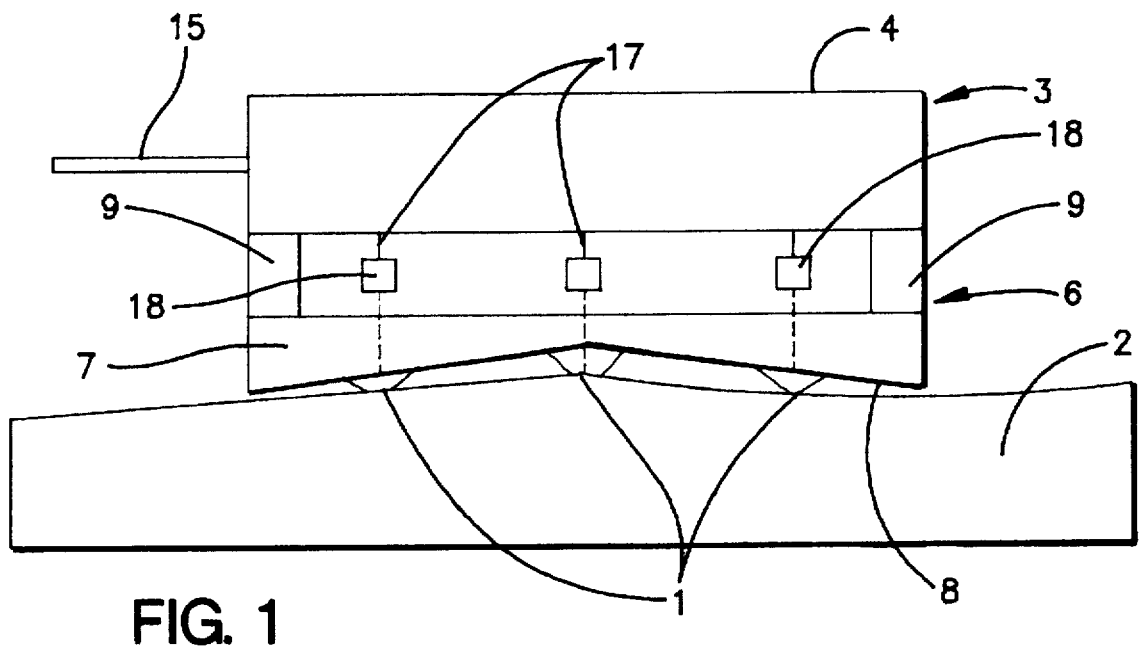
FIG. 1 is a schematic view in side elevation of the detector device according to the invention.
Figure 2:
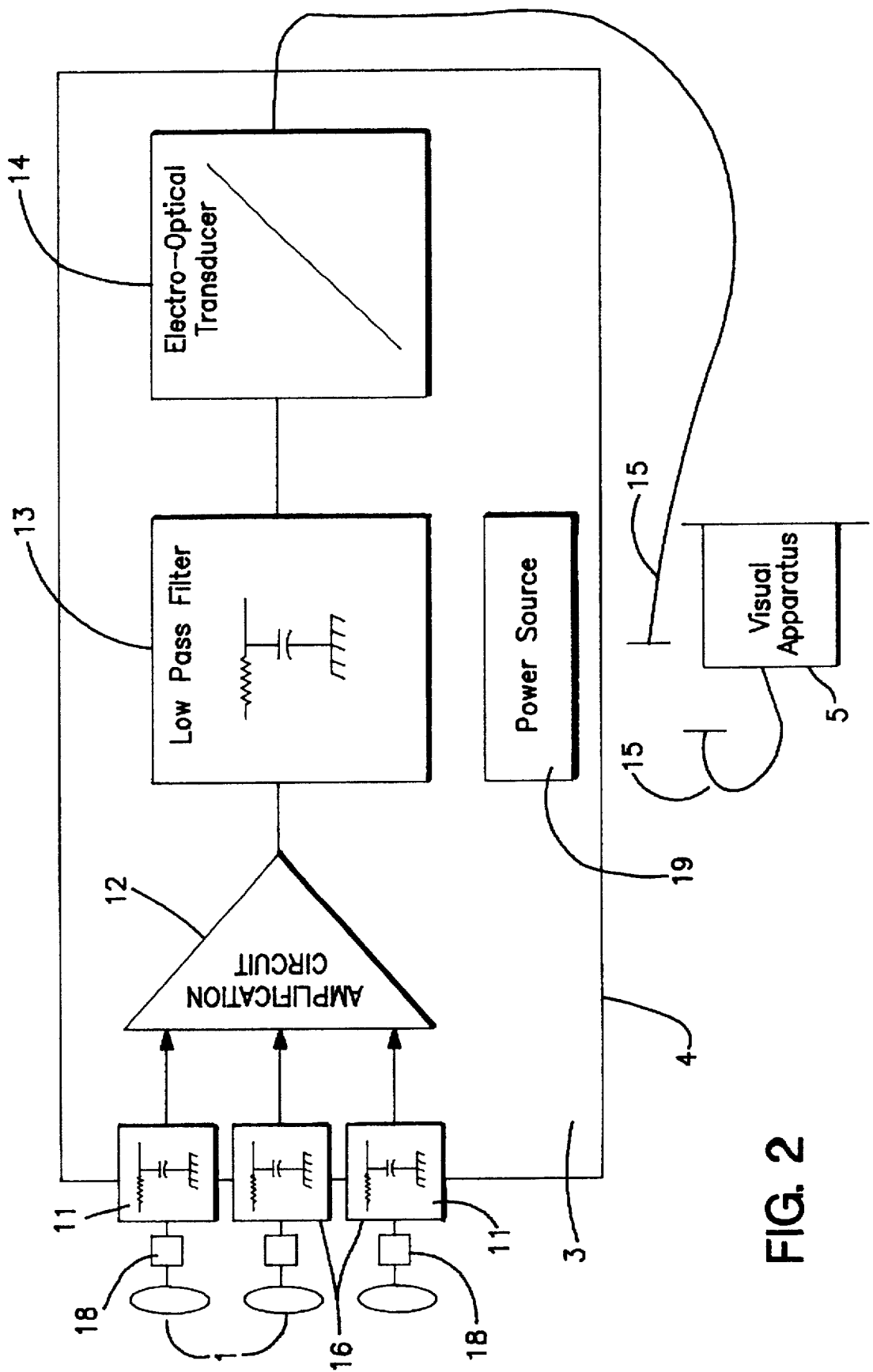
FIG. 2 is a functional schematic diagram of the detector device shown in FIG. 1.

According to the invention and as shown in FIGS. 1 and 2 of the attached drawings, the detector device is principally constituted, on the one hand, by at least two non-metallic electrodes 1 adapted to be applied to the skin of a patient 2, on the other hand by a module 3 for filtering and amplifying and electro-optically converting electric signals from the heart received by means of the receiving electrodes 1, disposed in a shielded housing 4 forming a Faraday cage and connected by optical means to an apparatus 5 for visualization and/or control and, finally, by a support body 6 of an amagnetic material, carrying the electrodes 1 and the shielded housing 4 containing the module 3.

The electrocardiograph signals received by the electrodes 1 are, as a result, immediately amplified and filtered with the aid of a suitable module 3, totally insulated from the external electromagnetic environment and, likewise, transformed and transmitted in optical form practically from their reception site.

According to a first characteristic of the invention, shown in FIG. 1 of the attached drawings, the support body 6 is comprised by a base 7 on which are mounted fixedly the receiving electrodes 1, protruding from the side 8 applied against the skin of the patient 2, and at least one separator or spacing element 9 maintaining rigidly the shielded housing 4 containing the module 3 at a constant distance from the base 7 and hence from the skin of the patient 2.

The sole metallic element of the detector device, namely the shielded housing 4, will not as a result ever be in direct contact with the patient 2, which avoids any risk of burning.

Moreover, the electrodes 1 being fixed on the base 7, the emplacement of these relative to each other is set by being spaced a distance which is a function of the size of the patient, and it suffices to position said base 7 adjacent the heart so that the electrodes 1 will be placed in a satisfactory manner.

The support body 6 can preferably be made of a material such as Teflon or polymethyl methacrylate (also known under the term "plexiglass"), having a rounded structure without ridges.

Likewise, the electrodes 1, preferably three in number, are preferably formed of a conductive material selected from the group formed by carbon, carbon compounds and plastic materials and insensitive to electromagnetic fields.

Figure 3:
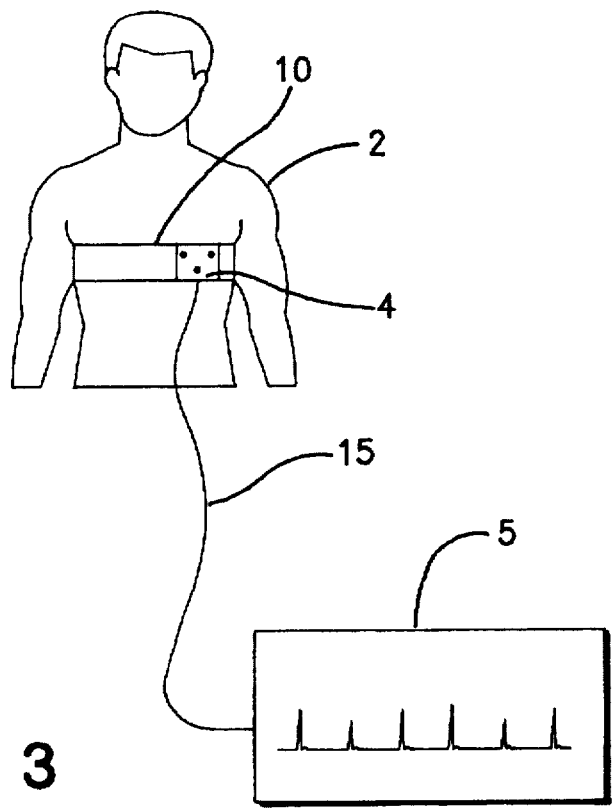
FIG. 3 is a schematic representation showing the use of the detector device shown in FIG. 1.

According to a preferred embodiment of the invention, shown in FIG. 3 of the attached drawings and so as to ensure a firm positioning of the electrodes 1 and to guarantee receipt of cardiac electric signals as close as possible to the heart, there is provided a belt 10 or a harness of an amagnetic material, if desired elastic, provided with quick means for closure and for adjustment of the length and passing through the support body 6 or at least an arm fixed to said support body 6.

Thus, the base 7 of the support body 6 and thus the electrodes 1 are permanently applied forcibly against the skin of the patient in the region of the heart.

However, any other suitable securement means could also be envisaged, provided it consists of an amagnetic material.

As shown in FIG. 2 of the attached drawings, the module 3 for filtering and amplification and conversion can be comprised, in essence, on the one hand, by high-frequency filter units 11 each associated with one of the electrodes 1, on the other hand by a differential amplification circuit 12 associated with a low-pass filter 13 and, finally, by an electro-optical transducer 14 connected by an optical conductor 15 to an apparatus 5 for visualization and/or control, the optical transmission of the signals being effected, for example, by frequency modulation or modulation of the pulse widths.

Each of the high-frequency filter units 11 ensuring the interface between the electrodes 1 and the module 3, could preferably be disposed in a shielded housing 16 forming a Faraday cage and the electrical connections between said electrodes 1 and the filter units 11 of the module 3 will be preferably comprised by rigid filaments 17 of short length, as the case may be shielded and each integrating a resistance limitation 18, limiting the interferences of the external electromagnetic waves and avoiding any formation of loops and risk of burning.

The differential amplification circuit 12 can have for example a gain of about 300 to 500 and one of the three electrodes 1 forming a part of the detector device according to the invention, could be used for the reinjection of the common mode (the two others functioning as receivers), permitting freedom from parasitic signals, particularly low frequency ones, received by the two receiving electrodes 1.

The filter 13 could preferably have a cutoff frequency of the order of 20 Hz.

The apparatus 5 for visualization and/or control could be disposed either in the enclosure of the NMR apparatus (Faraday cage), or outside the latter and will comprise an opto-electric reconversion unit, a screen for visualization and/or registration and/or a module for detection or analysis of the QRS complexes or of another parameter of the electrocardiogram signal, permitting triggering or controlling one or several apparatuses for analysis or visualization and/or for testing the patient.

The apparatus 5 could for example consist in a monitor for surveillance of the vital physiological parameters of a patient in the course of said NMR examination, of the type of that which is the object of French application No. 9014846 of Nov. 23, 1990 in the name of the applicant.

According to a first modified embodiment of the invention, the module 3 comprises also, for its electrical supply, a battery 19 or a rechargeable long length condenser of the amagnetic type, an optical conductor, associated with an optically controlled switch disposed in the housing, which can permit controlling the operation and supply of said module 3 for filtering and amplification and conversion and, as the case may be, the adjustment of the different components (11 to 14) of this latter (not shown).

According to a second modified embodiment of the invention, the energy supply of the module 3 for filtering and amplification and conversion is provided by means of an optical conductor coacting with a photovoltaic cell or like device disposed in the shielded housing 4.

Figure 4:
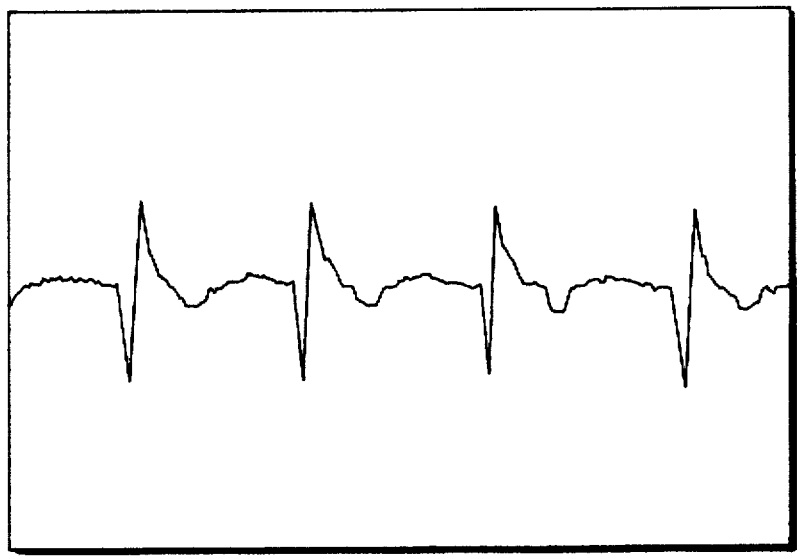
FIG. 4 represents an electrocardiogram signal obtained by means of a detector device according to the invention.
Figure 5:
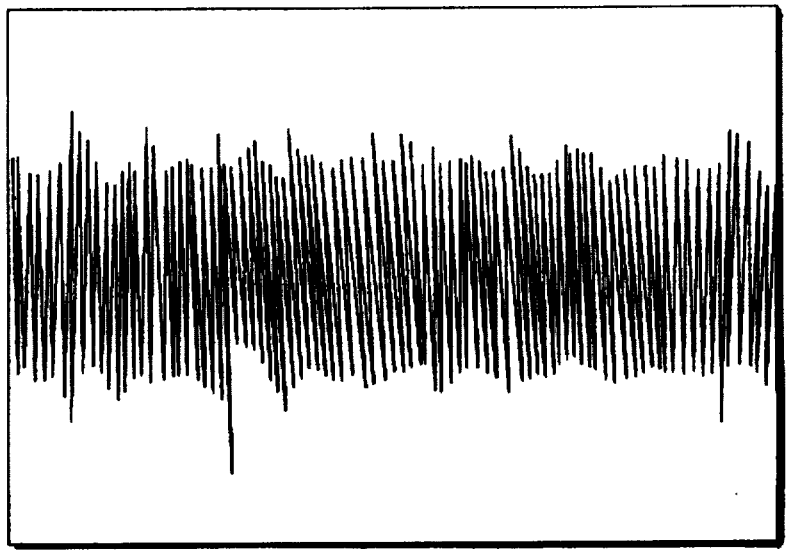
FIG. 5 represents an electrocardiogram signal obtained by means of a conventional detector, under conditions identical to those that produced the electrocardiogram of FIG. 4.

The improvement of the quality of the electrocardiogram signals received, resulting from the use of the invention, will be quite apparent by comparing the signal curves of FIGS. 4 and 5 with each other, these signals having been taken from patients subjected to NMR examination by means of a whole antenna body.

Of course, the invention is not limited to the embodiment described and shown in the accompanying drawing. Modifications remain possible, particularly as to the construction of the various elements or by the substitution of technical equivalents, without thereby departing from the scope of protection of the invention.

We claim:

1. In a detector device for electrocardiograms, adapted to be used in a loaded and sensitive electromagnetic environment, adjacent or within a nuclear magnetic resonance apparatus, and on a patient within the tunnel of the magnet of a magnetic resonance imager (MRI), the improvement wherein the device comprises at least two non-metallic electrodes for application to the patient's skin for receiving electrical signals from the heart; a module including means for filtering the electrical signals received from the heart, means for amplifying filtered signals, and means for electro-optically converting filtered and amplified electrical signals, said module being disposed in a shielded housing forming a Faraday cage; an optical means connecting said casing to an apparatus for visualization; and a support body of an amagnetic material carrying the shielded housing containing the module, said support body including means for maintaining the shielded housing at a constant distance from the patient's skin.

2. Detector device according to claim 1, wherein the support body includes a base having a side for application against the patient's skin, the electrodes being fixedly mounted on and projecting from said side, and said means for maintaining the shielded housing at a constant distance comprising at least one spacing element.

3. Detector device according to claim 1, wherein the electrodes are three in number, and are of a conductive material selected from the group consisting of carbon, carbon compounds and plastic materials.

4. Detector device according to claim 1, wherein the shielded housing is associated with a harness of an amagnetic material for securement to the patient's heart region.

5. Detector device according to claim 1, wherein the means for filtering comprise high-frequency filter units, each connected with one of the electrodes, the means for amplifying comprise a differential amplification circuit connected to a low-pass filter, and the means for electro-optically converting comprise an electro-optical transducer connected to an optical conductor to the apparatus for visualization.

6. Detector device according to claim 5, wherein the connections between the electrodes and the filter units comprise filaments of short length, each filament integrating a limitation resistance.

7. Detector device according to claim 5, wherein the device comprises three electrodes.

8. Detector device according to claim 1, wherein the module further comprises a power source selected from the group comprised of a battery and a rechargeable long-duration amagnetic condenser, and an electrical conductor associated with an optically controlled switch disposed in the housing for controlling the operation and the supply of said module and the adjustment of its components.

9. Detector device according to claim 1, wherein the module is supplied with energy provided by means of an optical conductor operatively associated with a photovoltaic cell disposed in the shielded housing.

* * * * *